United States Patent
O'Brien et al.

(10) Patent No.: US 9,999,870 B2
(45) Date of Patent: Jun. 19, 2018

(54) NANOSTRUCTURED SOLAR SELECTIVE CATALYTIC SUPPORTS

(71) Applicants: Paul Gregory O'Brien, Toronto (CA); Geoffrey Alan Ozin, Toronto (CA)

(72) Inventors: Paul Gregory O'Brien, Toronto (CA); Geoffrey Alan Ozin, Toronto (CA)

(73) Assignees: Paul Gregory O'Brien, Toronto, Ontario (CA); Geoffrey Alan Ozin, Toronto, Ontario (CA)

( * ) Notice: Subject to any disclaimer, the term of this patent is extended or adjusted under 35 U.S.C. 154(b) by 475 days.

(21) Appl. No.: 14/484,921

(22) Filed: Sep. 12, 2014

(65) Prior Publication Data

US 2016/0074833 A1 Mar. 17, 2016

(51) Int. Cl.
*B01J 21/06* (2006.01)
*B01J 23/46* (2006.01)
(Continued)

(52) U.S. Cl.
CPC ............ *B01J 21/06* (2013.01); *B01J 12/007* (2013.01); *B01J 19/123* (2013.01); *B01J 19/127* (2013.01); *B01J 19/128* (2013.01); *B01J 23/462* (2013.01); *B01J 35/004* (2013.01); *B01J 35/06* (2013.01); *B01J 37/347* (2013.01); *C07C 1/12* (2013.01); *B01J 35/0013* (2013.01); *B01J 35/023* (2013.01); *B01J 37/06* (2013.01); *B01J 2219/0877* (2013.01); *B01J 2219/0883* (2013.01); *B01J 2219/0884* (2013.01);
(Continued)

(58) Field of Classification Search
CPC ........ B01J 21/06; B01J 23/462; B01J 23/755; B01J 35/0006; B01J 35/004; B01J 35/023; B01J 19/123; B01J 19/127; B01J 19/128; C07C 1/12
See application file for complete search history.

(56) References Cited

U.S. PATENT DOCUMENTS

| 7,476,607 B2 * | 1/2009 | Yamada | ................. B01J 35/004 136/248 |
| 7,777,291 B2 * | 8/2010 | Kabir | .................... B01J 23/755 257/16 |

(Continued)

OTHER PUBLICATIONS

Agnihotri, O.P., et. al., "Solar Selective Surfaces", John Wiley & Sons, Inc., 1981, 88-191.
(Continued)

*Primary Examiner* — Cam N. Nguyen
(74) *Attorney, Agent, or Firm* — Norton Rose Fulbright Canada LLP

(57) ABSTRACT

A combined catalyst and catalyst support comprising: a nanostructured solar selective support to which at least one catalyst is affixed; the catalyst comprising at least one material that activates chemical reactions that produce fuels; the nanostructured solar selective support comprising material that is highly absorbing over a portion of the solar spectrum and exhibits low emissivity toward thermal radiation and/or has a surface textured to lower emissivity; the combined catalyst and catalyst support exhibiting at least one of a photochemical effect and a photothermal effect; wherein these effects cause the chemical reaction rates to increase with exposure to an increasing number of incident photons within the solar spectrum.

20 Claims, 9 Drawing Sheets

(51) Int. Cl.

| | |
|---|---|
| *B01J 23/755* | (2006.01) |
| *B01J 35/00* | (2006.01) |
| *B01J 35/02* | (2006.01) |
| *B01J 19/12* | (2006.01) |
| *C07C 1/12* | (2006.01) |
| *B01J 12/00* | (2006.01) |
| *B01J 37/34* | (2006.01) |
| *B01J 35/06* | (2006.01) |
| *C10L 3/08* | (2006.01) |
| *B01J 37/06* | (2006.01) |

(52) U.S. Cl.
CPC ... *B01J 2219/0892* (2013.01); *C07C 2521/06* (2013.01); *C07C 2523/46* (2013.01); *C10L 3/08* (2013.01)

(56) References Cited

U.S. PATENT DOCUMENTS

| | | | | |
|---|---|---|---|---|
| 8,183,659 | B2* | 5/2012 | Kabir | B01J 23/755 257/16 |
| 8,415,787 | B2* | 4/2013 | Kabir | B01J 23/755 257/16 |
| 9,205,420 | B2* | 12/2015 | Reece | B01J 19/127 |
| 2008/0223713 | A1* | 9/2008 | Xu | B01D 53/8668 204/157.15 |
| 2009/0264277 | A1* | 10/2009 | Raj | B01J 21/08 502/4 |
| 2010/0133111 | A1* | 6/2010 | Nocera | H01M 14/005 205/633 |
| 2011/0053020 | A1* | 3/2011 | Norton | B01J 21/063 429/425 |
| 2012/0007028 | A1* | 1/2012 | Hwang | H01M 4/134 252/503 |
| 2015/0090937 | A1* | 4/2015 | Idriss | B01J 37/16 252/372 |

OTHER PUBLICATIONS

J.A. De Gouw, et al., "Reduced Emissions of CO2, NOx, and SO2 from U.S. Power Plants Owing to Switch from Coal to Natural Gas with Combined Cycle Technology", Earth's Future, 2014, 2 : 75-82.
Donald, et. al., "Absolute Standard Hydrogen Electrode Potential Measured by Reduction of Aqueous Nanodrops in the Gas Phase", J. Am. Chem. Soc., 130, 2008, 3371-3381.
Foley, "Global Carbon Emissions Projected to Reach Record High in 2013", Nature World News, Nov. 19, 2013.
S.N. Habisreutinger, et al., "Photocatalytic Reduction of CO2 on TiO2 and Other Semiconductors", Angew. Chem. Int. Ed., 52, 2013, 2-39.
G.L. Harding, "Sputtered Metal Carbide Solar-Selective Absorbing Surface", J. Vac. Sci. Technol. 13, 1976, 1070-1072.
G.L. Harding, "Sputtered Metal Silicide Solar Selective Absorbing Surfaces", J. Vac. Sci. Technol. 15, 1978, 65-69.
A. Harriman, "Prospects for Conversion of Solar Energy into Chemical Fuels: the Concept of a Solar Fuels Industry", Philosophical Transactions of the Royal Society A, 2013, 1-16.
L.B. Hoch, et al., "The Rational Design of a Single-Component Photocatalyst for Gas-Phase CO2 Reduction Using Both UV and Visible Light", Adv. Sci., 1, 2014, 1-10.
H-C Hsu, et al., "Graphene Oxide as a Promising Photocatalyst for CO2 to Methanol Conversion", Nanoscale, 5, 2013, 262-268.

Y. Izumi, "Recent Advances in the Photocatalytic Conversion of Carbon Dioxide to Fuels with Water and/or Hydrogen Using Solar Energy and Beyond", Coordination Chemistry Reviews, 257, 2013, 171-186.
J. Kim, et al., "Methanol Production from CO2 Using Solar-Thermal Energy: Process Development and Techno-Economic Analysis", Energy & Environmental Science, 4, 2011, 3122-3132.
J. Kim, et al., "Fuel Production from CO2 Using Solar-Thermal Energy: System Level Analysis", Energy & Environmental Science, 5, 2012, 8417-8429.
M.M. Koltun, "Selective Optical Surfaces for Solar Energy Converters", Allerton Press, Inc., 1981, 122-149.
A. Lattes, "The Independent Chemist", Chemistry International, Sep.-Oct. 2013, 7-10.
C-C Lo, et al., "Photoreduction of Carbon Dioxide with H2 and H2O Over TiO2 and ZrO2 in a Circulated Photocatalytic Reactor", Solar Energy Materials & Solar Cells, 91, 2007, 1765-1774.
J. Melsheimer, et al., "Methanation of Carbon Dioxide Over Ru/Titania at Room Temperature: Explorations for a Photoassisted Catalytic Reaction", Catalysis Letters, 11, 1991, 157-168.
X. Meng, et al., "Photothermal Conversion of CO2 into CH4 with H2 over Group VIII Nanocatalysts: An Alternative Approach for Solar Fuel Production", Angew. Chem., 126, 2014, 11662-11666.
S. Navalon, et al., "Photocatalytic CO2 Reduction Using Non-Titanium Metal Oxides and Sulfides", ChemSusChem, 6, 2013, 562-577.
S. Neatu, et al., "Solar Light Photocatalytic CO2 Reduction: General Considerations and Selected Bench-Mark Photocatalysts", Int. J. Mol. Sci., 15, 2014, 5246-5262.
K. Ogura, et al., "Dark Catalytic Reduction of CO2 Over Photo-Pretreated NiO/ksgr Catalyst", Journal of Molecular Catalysis, 72, 1992, 173-179.
G.A. Olah, et al., "Anthropogenic Chemical Carbon Cycle for a Sustainable Future", J. Am. Chem. Soc., 133, 2011, 12881-12898.
R.B. Pettit, et al., "Solar Absorptance and Emittance Properties of Several Solar Coatings" J. Vac. Sci. Technol., vol. 13, No. 2, 1976. 596-602.
R.J. Powell, et al., "Optical Properties of NiO and CoO", Physical Review B, vol. 2, No. 6, Sep. 15, 1970, 2182-2193.
C. Revilliod, et al., "High Intensity Simulated Solar Irradiation: Effect on the Kinetics of a Methanation Reaction", Solar Energy Materials, 24, 1991, 522-537.
F. Sastre, et al., "Complete Photocatalytic Reduction of CO2 to Methane by H2 under Solar Light Irradiation", J. Am. Chem. Soc., 136, 2014, 6798-6801.
A. Steinfeld, et al., "Solar Thermochemical Process Technology", Encyclopedia of Physical Science & Technology, R.A. Meyers Ed., American Press, vol. 15, 2001, 237-256.
K. Teramura, et al., "Photocatalytic Reduction of CO2 in the Presence of H2 or CH4 as a Reductant over MgO", J. Phys. Chem. B, 108, 2004, 346-354.
K. Teramura, et al., "Effect of H2 Gas as a reductant on Photoreduction of CO2 over a Ga2O3 Photocatalyst", Chemical Physics Letters, 467, 2008, 191-194.
K. R. Thampi, et al., "Methanation and Photo-Methanation of Carbon Dioxide at Room Temperature and Atmospheric Pressure", Nature, vol. 327, Jun. 11, 1987, 506-508.
M. Van Der Leij, "Investigation and Perspectives on Iron Oxide, Zinc Conversion Coating, Zinc Oxide, Cobalt Oxide and Tungsten Oxide as Spectral Selective Solar Absorber Surfaces", 837-841.
C-C Yang, et al., "Artificial Photosynthesis over Crystalline TiO2-Based Catalysts: Fact or Fiction?", J. Am. Chem. Soc., 132, 2010, 8398-8406.
S. Yoshida, et al., "A New Type of Photocatalysis Initiated by Photoexcitation of Adsorbed Carbon Dioxide on ZrO2", Catalysis Surveys from Japan, Vo. 4, No. 2, 2000, 107-114.

* cited by examiner

NANOSTRUCTURED SOLAR SELECTIVE CATALYTIC SUPPORTS

FIELD OF THE INVENTION

The invention relates to nanostructured solar selective surfaces for supporting catalysts that use solar energy to activate chemical reactions.

BACKGROUND OF THE INVENTION

Due to intensified economic and environmental consequences of burning fossil fuels, increasing amounts of research have been directed towards using radiant solar energy to catalyze or power solar fuels reactions (Steinfeld, R. Palumbo, "Solar Thermochemical Process Technology" in Encyclopedia of Physical Science and Technology; R. A. Meyers Ed., Academic Press, BVol. 15, pp. 237-256, 2001; Kim et. al. Energy Environ. Sci., 5, 8417, 2012; Kim et. al. Energy Environ. Sci., 4, 3122, 2011; Harriman, Phil. Trans. R. Soc. A 371, 20110415, 2013). The environmental problems associated with burning fossil fuels stem from the emission of greenhouse gases. For every ton of burned carbon 3.67 tons of $CO_2$ are released into the atmosphere and $CO_2$ emissions from burning fossil fuels continue to rise and reached almost 40 Gt in 2013 (Foley, "Global Carbon Emissions Projected to Reach Record High in 2013" Nov. 19, 2013 in Nature World News). Meanwhile the radiant solar energy impinging on the earth's surface over one hour is greater than the world's annual energy usage and an alternative solution to the impending energy and climate crises is to make solar fuels from the suns energy rather than continue to deplete legacy fossil fuels from the earth (Izumi, Coord. Chem. Rev. 257, 171, 2013, Neatu et. al., Int. J. Mol. Sci. 15, 5246, 2014, Habisreutinger et. al. Angew. Chem. Int. Ed. 52, 7372, 2013, Navalon et. al., ChemSusChem. 6, 562, 2013).

The concept of solar fuels is based on harnessing an abundant supply of energy from the sun and storing it in the form of chemical bonds as energy rich transportable fuels and chemical feed stocks. The most common solar fuel investigated in the literature is hydrogen gas generated from solar powered water splitting. Other solar fuel reactions involving the reduction of $CO_2$ to generate carbon-based fuels and chemicals, such as carbon monoxide (CO), methane ($CH_4$), and methanol ($CH_3OH$) offer another source of energy with neutral $CO_2$ emissions. Other reactions that reduce $CO_2$ to useful fuels in a hydrogen environment under solar irradiation may be considered as a complementary solar fuels reaction. For example, the Sabatier reaction reduces $CO_2$ to $CH_4$ in a hydrogen environment. This reaction is not a direct solar fuels reaction because it does not increase the amount of energy stored in chemical bonds whether or not it is activated under solar irradiation. However, when coupled with a solar powered water-splitting reaction it can simultaneously reduce greenhouse gas emissions and provide methane to natural gas pipeline networks. Furthermore, $CO_2$ reduction reactions in the gas-phase, rather than in the liquid phase, are expected to provide the most practical and economically feasible route to large-scale solar fuels operations (Olah et. al. J. Am. Chem. Soc., 133, 12881, 2011). In fact, over the last decade increasing amounts of natural gas have been produced through advances in directional drilling and hydraulic fracturing and natural gas power plants have led to reduced emissions of $CO_2$, $NO_x$ and $SO_2$. Thus, as shown in FIG. 9, the solar powered photomethanation of $CO_2$ using a renewable source of $H_2$ is a present-day solution that can simultaneously reduce greenhouse gas emissions and also provide methane to natural gas pipeline networks (Lattes, Chemistry International, 35, 5, p. 7-10, ISSN (Online) 1365-2192, ISSN (Print) 0193-6484, DOI: 10.1515/ci-2013-0504, May 2014; de Gouw et. al., Earth's Future, 2: 75, 2014).

Gas phase photomethanation of $CO_2$ with $H_2$ was initially reported using a catalyst comprised of dispersed Ru—$RuO_x$ on $TiO_2$ (Thampi et. al., Nature. 327, 506, 1987). Enhanced methanation rates were originally attributed to the chemical effects of electron-hole pairs generated from UV-light absorption in the $TiO_2$ support. However, subsequent studies revealed that photoactive species adsorbed on the catalyst surface (Revilliod et. al., Sol. Energ. Mater. 24, 522, 1991) as well as the increased temperature of the catalyst under light irradiation (Melsheimer et. al., Catal Lett. 11, 157, 1991) played a more significant role in increasing the methanation rates rather than the direct band-gap absorption of the $TiO_2$ support. Since this initial study, numerous catalysts have been tested for photoactivated $CO_2$ reduction with $H_2$. For example, Yoshida et. al. tested $TiO_2$, $ZrO_2$, $V_2O_5$, $Nb_2O_5$, $Ta_2O_5$, $WO_3$, and ZnO and found that of these materials, only $ZrO_2$ exhibited photoactivity for the reduction of $CO_2$ to CO in a $H_2$ atmosphere (Yoshida et. al., Catal Surv Jpn, 4, 2, 2000). In a following study, the photoreduction of $CO_2$ to CO using $H_2$ gas was also observed on the surface of a MgO catalyst (Teramura et. al. J. Phys. Chem. B., 108, 346-354, 2004). The reaction mechanisms for both the MgO and $ZrO_2$ catalysts involved the photoexcitation of carbonaceous species adsorbed on the catalyst surface. Furthermore, Lo et. al. also demonstrated the photoreduction of $CO_2$ over $ZrO_2$ in a circulating photocatalytic reactor (Lo et. al., Sol. Energ. Mat. Sol. C., 91, 1765, 2007). More recently, $CO_2$ photoreduction to methanol has been reported to occur over Graphene Oxide (GO) catalysts (Hsu et. al. and, L. C. Chen, Y. C. Lin, K. H. Chen, Nanoscale, 5, 262, 2013). The absorption edge of the GO catalyst was at least 3.2 eV and it was proposed that the reaction mechanism involves photogenerated electrons and holes migrating to the GO surface and reacting with adsorbed $CO_2$ and $H_2O$ to produce methanol. $CO_2$ photoreduction to methanol was also reported over zinc-copper-gallium layered double hydroxides (K. Teramura et. al. Chem. Phys. Lett. 467, 191, 2008) and it was suggested that $CO_2$ reacted with hydroxyl groups bound to Cu to form hydrogen carbonate which subsequently decomposed in an $H_2$ atmosphere under UV-Visible light. Moreover, very recently Hoch et. al. have shown that hydroxylated indium oxide nanoparticles with a bixbyite crystal structure and forbidden electronic band gap are active for the photoreduction of $CO_2$ to CO. The proposed reaction mechanism involves oxygen vacancies and hydroxides at the surface of the nanoparticles to reduce $CO_2$ (Hoch et. al., submitted for publication 2014).

In general, when testing catalysts for the photoactive reduction of $CO_2$ it is important to ensure that the products do not originate from adventitious carbon sources (C. Yang, J. Am. Chem. Soc., 132, 8398, 2010). In this context, isotope tracing experiments using Fourier-Transform Infra-Red (FTIR) spectroscopy and Mass Spectroscopy (MS) are particularly effective (Y. Izumi, Coordin. Chem. Rev. 257(1), 171-186, 2013). Further, it is interesting to note that $CO_2$ photoreduction rates reported in the literature for catalysts tested using isotope tracing experiments are on the order of 1 μmol/gcat·h or less, orders of magnitude below that required for the technological development of a practical large scale $CO_2$ photoreduction process. However, very recently these poor performance metrics were broken when Sastre et. al. reported the complete photocatalytic reduction of $CO_2$ to methane in $H_2$ using a catalyst comprised of Ni on a silica-alumina support (Sastre et. al., J. Am. Chem. Soc. 136, 6798-6801, 2014). The complete methanation of $CO_2$ reported in this work infers a $CO_2$ photoreduction rate well over 10 mmol/gcat·h. It was proposed that the reaction mechanism involves photogenerated electrons (holes), reducing (oxidizing) $H_2$ to form Ni—H which then functions as the active $CO_2$ reducing agent. Moreover, by performing experiments with optical filters it was determined that 76% of the photoreduction of $CO_2$ was activated using UV light, which is consistent with the photon energy required to excite electrons across the 3.8 eV bandgap of NiO (R. J. Powell et. al., Phys. Rev. B2, 2182, 1970). It is also noteworthy that this proposed mechanism is reinforced by previous experiments reporting the methanation of $CO_2$ over NiO-based catalysts that were pre-treated in an $H_2$ atmosphere under UV-light. (K. Ogura, et. al., J Mol Catal. 72, 173-179, 1992). In this regard it is noteworthy that the photon energy required to excite electrons across the ~3.8 eV bandgap of NiO is about 330 nm. In another set of experiments recently reported in the literature it is shown that the Sabatier reaction on Ru-based catalysts with $Al_2O_3$ supports proceeds photothermally. Furthermore, the results from this study show that the Ru-based catalyst with an $Al_2O_3$ support does not exhibit any photochemical activity (Meng et. al., Angew. Chem. 2014, 126, 1-6).

Note that in all the aforementioned research the support was absorbing in the ultraviolet wavelength region of the solar spectrum but transparent to the rest of the solar spectrum in the visible and infrared range and therefore distinct to a solar selective catalyst support which is the central focus of the invention described herein.

All references listed herein are incorporated by reference herein in their entireties.

SUMMARY OF THE INVENTION

This description relates to combined catalyst and catalyst support comprising: a nanostructured solar selective support to which at least one catalyst is affixed; the catalyst comprising at least one material that activates chemical reactions that produce fuels; the nanostructured solar selective support comprising material that is highly absorbing over a portion of the solar spectrum and exhibits low emissivity toward thermal radiation and/or has a surface textured to lower emissivity; the combined catalyst and catalyst support exhibiting at least one of a photochemical effect and a photothermal effect; wherein these effects cause the chemical reaction rates to increase with exposure to an increasing number of incident photons within the solar spectrum.

The chemical reaction may be selected from the group consisting of Sabatier reaction, methanol synthesis, reverse water gas shift, methane synthesis, carbon dioxide splitting, water gas shift, Fischer-Tropsch synthesis, water splitting, reverse Boudard reaction, dry reforming of methane, bi-reforming of methane and the Carnol process. The nanostructured solar selective surface may comprise at least one material selected from the group consisting of black silicon, black carbon, black nickel, black cobalt, black chrome, black copper, black iron, black zinc, tungsten oxide, metal silicides, and carbides.

In one form, the nanostructured solar selective surface may be selected from a semiconductor chosen from the group consisting of germanium, silicon, stoichiometric and non-stoichiometric metal oxides and metal sulfides; a nanostructured solar selective support made with a pigmented selective paint; a nanostructured silicon film made from a silicon wafer with nanowires etched into its surface; an inverted silicon opal with an air-hole diameter ranging from approximately 50 nm to 500 nm; a film comprised of silicon nanoparticles having a diameter on the order of magnitude of 100 nm; a hydrogenated amorphous silicon film deposited onto a nanostructured surface; and a silicon top surface of a photonic crystal comprising nanoscale spheres, wires, rods, tubes or nanoscale pores. The surface of the semiconductor support, the metallic particles or both may be partially or fully oxidized.

In another form, the nanostructured solar selective support may be made of porous silicon with an interconnected framework of pores that have a diameter on the order of 100 nm or it may be made from Si or $SiO_x$ nanoparticles, where x is less than 2.

The catalyst may be deposited on the support using a method selected from the group consisting of chemical vapour deposition, metal organic chemical vapour deposition, atomic layer deposition, electron beam deposition, solid phase crystallization, sputtering, wet impregnation, electrodeposition, electroless deposition, spray coating, pulsed laser deposition, electrospinning, sol-gel processes, spin-coating, dip-coating, and drop-casting.

In another form, the catalyst comprises particles consisting of one or more metals selected from the group consisting of Sc, Ti, V, Cr, Mn, Fe, Co, Ni, Cu, Zn; Y, Zr, Nb, Mo, Ru, Rh, Pd, Ag, Cd, La, Hf, Ta, W, Os, Ir, Pt, and Au.

In another form, the catalyst affixed to the support may be a molecular complex.

In yet another form, the catalyst affixed to the support may be chosen from stoichiometric and non-stoichiometric main group, transition group, lanthanide and actinide group, oxides, sulfides, selenides, tellurides, phosphides, borides, carbides, nitrides, silicides, and halides and mixtures thereof.

In another form, the catalyst affixed to the support may have a shape selected from the group consisting of solid and hollow versions of spherical, cylindrical, disks, platelets, rhombic, elongated rhombic, hexagonal, square, triangular, tetrahedral, octahedral and pyramidal shapes.

In one specific form, the catalyst affixed to the support may be Ru or Ni particles and the catalyst support is black silicon nanowires etched into a silicon wafer. In another form, the catalyst support is a semiconductor with conduction and valence band energies that are about 3.5 to 4.25 eV and 4.7 to 5.5 eV below the vacuum energy level, respectively.

In yet another form, the catalyst support may be a semiconductor with a band-gap energy between 0.3 eV and 2.5 eV.

The support may reside at the focal point of a solar concentrator during operation.

DETAILED DESCRIPTION OF THE INVENTION

This description and drawings are illustrative of the catalyst support and catalyst and are not to be construed as limiting the disclosure. Numerous specific details are described to provide a thorough understanding of various embodiments of the present disclosure. However, in certain circumstances, well-known or conventional details are not described in order to provide a concise discussion.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are include. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

As used herein, the phrase "within an order of magnitude" is meant to imply that the actual number is approximately ten times higher or ten times lower that the number provided.

Unless defined otherwise, all technical and scientific terms used herein are intended to have the same meaning as commonly understood to one of ordinary skill in the art.

Definitions

Catalyst Support refers to a solid material to which a catalyst can be affixed.

Solar Selective Surface is a surface that is highly absorbing towards solar radiation (with an average absorption greater than ~80% over wavelengths ranging from ~300 nm to ~2500 nm) and has a low emissivity towards thermal radiation (such that its overall thermal emissivity is less than ~0.35).

Nanoscale Pores are pores with a width, depth or height of approximately 1 nm to 100 nm.

Nanoscale surface Textures refers to grooves, pyramids, wires, pits, holes, pores or other features on a surface that have a length, width or height of approximately 1 nm to 100 nm.

Highly Absorbing Black Surface is a surface that highly absorbs solar radiation (greater than ~80% over most of the spectral region ranging from 300 nm to 2500 nm) and appears to be black or dark brown in colour.

Emissivity of a surface ranges from 0 to 1 and is the ratio of how effectively it emits thermal radiation in comparison to a perfectly emitting black body.

Nanostructured refers to an object or surface that has been made to have geometrical features on the nanoscale, which refers to lengths of approximately 1 to several hundred nanometers.

Nanowire is a nanostructure with a diameter ranging from ~1 nm to ~100 nm and a length of one µm or more.

Inverted opal: Opaline photonic crystals are formed when dispersions of glass or polymeric microspheres self-assemble into an ordered or disordered structure as the dispersion evaporates. An inverted opal is formed by infiltrating the void space between the spheres with a material such as silicon and then subsequently removing the spheres.

Porous silicon refers to a silicon wafer with an interconnected network of ordered or disordered pores that have a height, length, width or diameter ranging between approximately 1 nm and several hundred nanometers.

Nanoparticle refers to a particle with length, height or width on the order of approximately 0.5 nm to 100 nm.

Photothermal Effect refers to the heat or thermal energy generated in a material when an incident photon is absorbed within this material. When a chemical reaction rate is increased photothermally the energy of the absorbed photons is converted to heat and this heat in turn accelerates the reaction.

Photochemical Effect refers to the increase in the chemical potential of an electron, hole, phonon, or other species in a material caused by the absorption of an incident photon. When a chemical reaction rate is increased photochemically the increased chemical potential of the aforementioned species within the material provides a source of energy that activates the chemical reaction.

Nanostructured solar selective catalytic supports (NS-SCS) exhibit a unique combination of properties that are ideal for hosting solar powered chemical reactions. Specifically, they are highly absorbing over a broad portion of the solar spectrum, their emissivity is significantly reduced compared to that of a black-body, they can be electronically doped to form high quality electrical connections and/or junctions with catalysts loaded onto their surface, they have good thermal heat conduction and they may have conduction and valence band energies that straddle $H_2/H^+$ redox potentials (Donald et. al., J. Am. Chem. Soc., 130, 3371, 2008).

The nanostructured catalytic supports disclosed herein have a solar selective surface, i.e. their surfaces are highly absorbing over a portion of the solar spectrum (from ~300 nm to ~2500 nm) but exhibit a low emissivity towards thermal radiation. Semiconductor catalytic supports are highly absorbing over the solar spectral region wherein the incident photons have energy greater than the band-gap of the semiconductor. For example, supports made from silicon with a band-gap of 1.1 eV are highly absorbing over the solar spectral region ranging from ~300 nm to 1100 nm, which represents ~85% of the solar irradiance. As another example, supports made from a semiconductor with a band-gap of 2.5 eV are highly absorbing over the spectral region ranging from 300 nm to 500 nm, which represents ~25% of the solar irradiance. Supports made from other materials may be highly absorbing over the entire solar spectral region.

Types of selective coatings that absorb in the solar spectrum and exhibit low emissivity towards thermal radiation include black oxides of metals deposited onto metal substrates, doped semiconductors, metal silicides, and selective paints comprised of semiconductor particles held together in an organic binder (M. M. Koltun, "Selective Optical Surfaces For Solar Energy Converters" 1981, Allerton Press, Inc.; R. B. Pettit, R. R. Sowell, "Solar Absorptance and Emittance Properties of Several Solar Coatings" J. Vac. Sci. Technol., Vol. 13, No. 2, 596, 1976; G. L. Harding, "Sputtered Metal Silicide Solar Selective Absorbing Surfaces" J. Vac. Sci. Technol. 15, 65 1978; G. L. Harding, "Sputtered Metal Carbide Solar-Selective Absorbing Surface" J. Vac. Sci. Technol. 13, 1070, 1976; M. van der Leij, Investigation and Perspectives on Iron Oxide, Zinc Conversion Coating, Zinc Oxide, Cobalt Oxide and Tungsten Oxide as Spectral Selective Solar Absorber Surfaces). This kind of selective support can be heated to hundreds of degrees under concentrated solar radiation and loose minimal amounts of heat energy through radiative losses on account of their low emissivity. They may be made from a material with low emissivity or their surface may be textured to lower their emissivity. Non-limiting examples of such surfaces include black nickel, black chrome, black copper, black iron and tungsten oxide as well as those of nanostructured and textured semiconductors such as silicon, germanium, and lead sulphide. (M. Vander Leij, Proc. ISES, New Delhi India, January, 1978; F. deWinter and M. Cox, Eds. Pergamon Press, New York, N.Y., 1978, p. 837; O. P. Agnihotri, B. K. Gupta, (1981) Solar Selective Surfaces, John Wiley & Sons, Inc.) Further, the surfaces of these supports may also be structured at the nanoscale in order to greatly increase their specific surface area and nano-sized catalysts are dispersed over the surface of these supports.

These nanostructured solar selective catalytic supports (NSSCS) may be formed with a continuous network of open pores, such as in the case of an inverted silicon opal or nanoporous silicon, or surface features may be etched into their surfaces to achieve a high surface area and optimal light trapping capabilities, such as in the case of black silicon nanowires. Due to their low reflectance and high absorption over the visible wavelength spectra they appear black or dark brown and can absorb as much as 99% of incident solar light over a broad spectral range from the ultraviolet through the visible to the infrared solar spectral range. On account of their high absorption over the solar spectrum (nanostructured solar selective catalytic supports) NSSCS are heated to high temperatures under concentrated solar irradiation. This heat is transferred to metallic or semiconducting catalysts loaded onto their surface in order to photothermally increase chemical reaction rates.

The electronic properties of (nanostructured solar selective catalytic supports) NSSCS may also be a key material property that functions to enhance chemical reaction rates. For example, a black nanostructured catalyst support made from a semiconductor can be electronically doped to form high quality electronic contacts or Schottky junctions with metallic and/or semiconductor catalysts loaded onto their surface. Solar photons absorbed in these nanostructured semiconducting supports can generate electron-hole pairs (EHPs). These excited charge carriers can then be transferred to active sites on the metallic or semiconducting catalysts loaded onto their surface to photochemically enhance chemical reaction rates.

One appropriate semiconductor is silicon. The electronic band gap of silicon is 1.1 eV while that of amorphous silicon ranges from ~1.5 eV to 2.0 eV depending on the method and conditions used during its fabrication process. Using black silicon nanowires as an example, with a band gap and optical absorption edge of 1.1 eV and 1100 nm, respectively, these nanostructured supports can absorb more than 85% of the solar irradiance to photothermally and photochemically drive chemical reactions. Moreover, on account of its optical band-gap, the emissivity of silicon is significantly reduced compared to that of a black-body. In this context, the ability to design and engineer nanostructured solar selective catalytic supports that utilize more than 85% of the solar irradiance to both photothermally and photochemically drive chemical reactions is unique to the silicon-based nanostructured supports disclosed herein.

Herein, as a non-limiting example of a catalyst affixed to a nanostructured solar selective catalytic support, there is disclosed the photomethanation of gas-phase $CO_2$ over Ru nanoparticles sputtered onto high surface area black silicon nanowire (SiNW) supports. Photomethanation rates over these Ru/SiNW catalyst are very high, on the order of 1 mmol/gcat·h when normalized to the weight of the Ru, and these rates can be greatly increased by optimizing the Ru nanoparticle dispersion over the SiNWs and using solar concentration. Moreover, regarding the chemical reaction mechanism, experimental results disclosed show that these Ru/SiNW catalysts photoactivate the Sabatier reaction both thermochemically and photochemically. That is, from a thermochemical standpoint, the Ru/SiNW catalyst heats up when irradiated with solar-simulated light and methanation rates increase due to increased local temperatures at the surface chemical reaction sites on the Ru/SiNW catalyst.

Additionally, regarding photochemical activation, the rate of the Sabatier reaction increases proportionally to the number of incident photons with energy greater than the band-gap of Si. It is noteworthy that, in contrast to the previously known NiO/silica-alumina and Ru/$Al_2O_3$ catalyst, the catalysts disclosed herein comprising nanostructured Si-based supports photochemically enhance Sabatier reaction rates using photons over a broad spectral range including UV, visible and NIR photons. Photochemical activity over a broad spectral range including the NIR over the catalysts disclosed herein can be attributed to the low band-gap energy of silicon compared to higher band-gap supports such as $SiO_2$ and $Al_2O_3$ exclusively utilized in the known art. Nanostructured silicon supports loaded with catalysts to photochemically activate reactions using photons over a broad spectral range including NIR photons has major implications for the design of a cornucopia of photothermally solar powered catalysts.

While the example provided herein demonstrates that the Sabatier reaction can be enhanced over Ru/SiNW catalysts, in general NSSCS can also be used to enhance the rate of relevant gas-phase solar fuels and complementary solar fuels reactions such as those listed below in Table 1.

TABLE 1

List of relevant reactions

| Equation No. | Equation Name | Equation |
|---|---|---|
| 1 | Methanol Synthesis | $CO_2 + 3H_2 \rightarrow CH_3OH + H_2O$ |
| 2 | Reverse Water Gas Shift | $CO_2 + H_2 \rightarrow H_2O + CO$ |
| 3 | Methane Synthesis | $CO_2 + 2H_2O \rightarrow CH_4 + 2O_2$ |
| 4 | Methanol Synthesis | $CO_2 + 2H_2O \rightarrow CH_3OH + 3/2O_2$ |
| 5 | Carbon Dioxide Splitting | $CO_2 \rightarrow CO + 1/2O_2$ |
| 6 | Water gas shift | $CO + H_2O \rightarrow CO_2 + H_2$ |
| 7 | Methanol Synthesis | $CO + 2H_2 \rightarrow CH_3OH$ |
| 8 | Fischer-Tropsch Synthesis: | $(2n + 1)H_2 + nCO \rightarrow C_nH_{2n} + 2 + nH_2O$ |
| 9 | Water Splitting | $2H_2O \rightarrow 2H_2 + O_2$ |
| 10 | Carnol Process | $3CH_4 + 2CO_2 \rightarrow 2H_2O + 2CH_3OH + 3C$ |
| 11 | Bi-Reforming of Methane | $3CH_4 + 2H_2O + 2CO_2 \rightarrow 4CO + 8H_2$ |
| 12 | Reverse Boudard Reaction | $CO_2 + C \rightarrow 2CO$ |
| 13 | Dry Reforming of Methane | $CH_4 + CO_2 \rightarrow 2CO + 2H_2$ |

BRIEF DESCRIPTION OF THE DRAWINGS

Exemplary embodiments of the combined catalyst and nanostructured solar selective catalyst supports will now be described, with reference to the drawings, in which:

FIG. 3(e) shows the absorption spectra for the polished Si, glass and SiNW supports with 10 nm of Ru sputtered onto their surface.

BLACK NANO-STRUCTURES COMPRISED OF SILICON

The electronic band gap of silicon is 1.1 eV while that of amorphous silicon ranges from ~1.5 eV to 2.0 eV depending on the method and conditions used during the fabrication process. The index of refraction of silicon has a peak value of almost 7 at a wavelength of 380 nm and decreases from about 4.5 at 500 nm to about 3.5 beyond 1100 nm. On account of this relatively high index of refraction polished silicon wafers exhibit high reflectivity (~40%) over the solar spectral region.

The reflection from silicon wafers can be greatly reduced by etching nanostructures into their surface. For example, by electrochemically etching a graded index porous silicon multilayer, reflectance has been reduced to below 5% over a broad spectral region from 360 nm to 3300 nm (Ma et. al. Appl. Phys. Lett. 88, 171907, 2006).

The broadband reflectance of a silicon wafer can be reduced even further by etching nanowires into its surface. These silicon nanowires have a height and width on the order of 10 μm and 200 nm, respectively. Further, the nanowires can be needle-shaped and form a graded effective medium that decreases from the bulk of the wafer to the outer surface of the nanowires. This creates a graded effective refractive index that reduces reflection (C. Tuck Choy (1999) Effective Medium Theory: Principles and Applications. Oxford University Press, Branz et al. Appl. Phys. Lett. 94, 231121, 2009).

Furthermore, it is also noteworthy that semiconductors with an electronic bandgap of approximately 1 eV are a suitable material for making a solar selective surface. For example, the emissivity of silicon is greatly reduced compared to that of a black-body for radiation with wavelengths longer than 1000 nm (T. Satō, Jpn. J. Appl. Phys., 6, 3, 1967).

Figure 1:
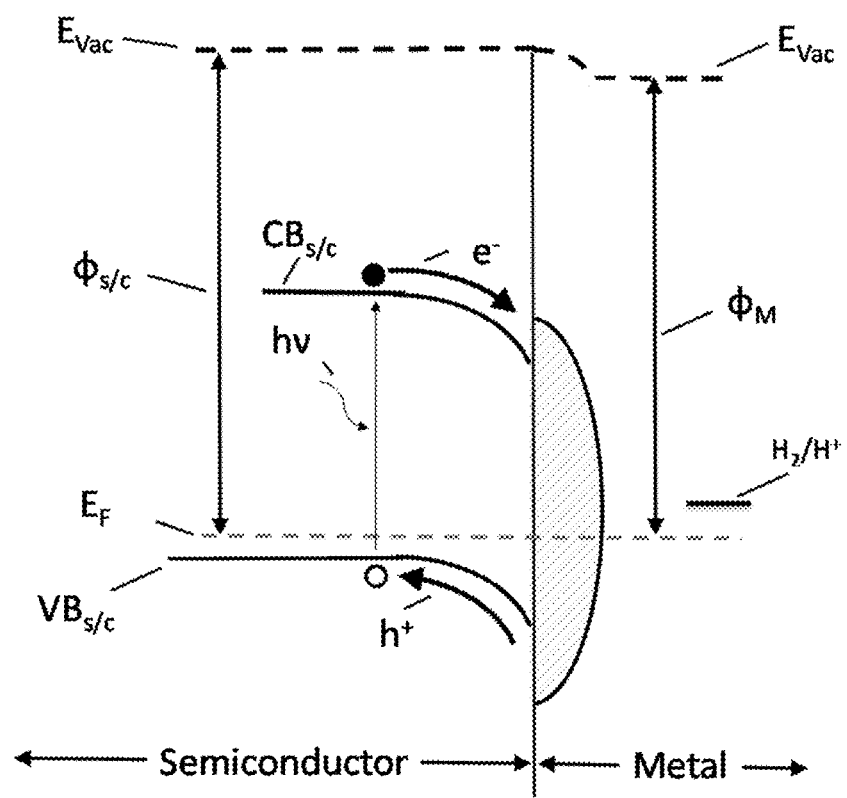
FIG. 1 shows a schematic diagram of an energy band diagram for a surface selective photo-thermal catalyst at the junction between a p-type semiconductor and a metal.
Figure 2:
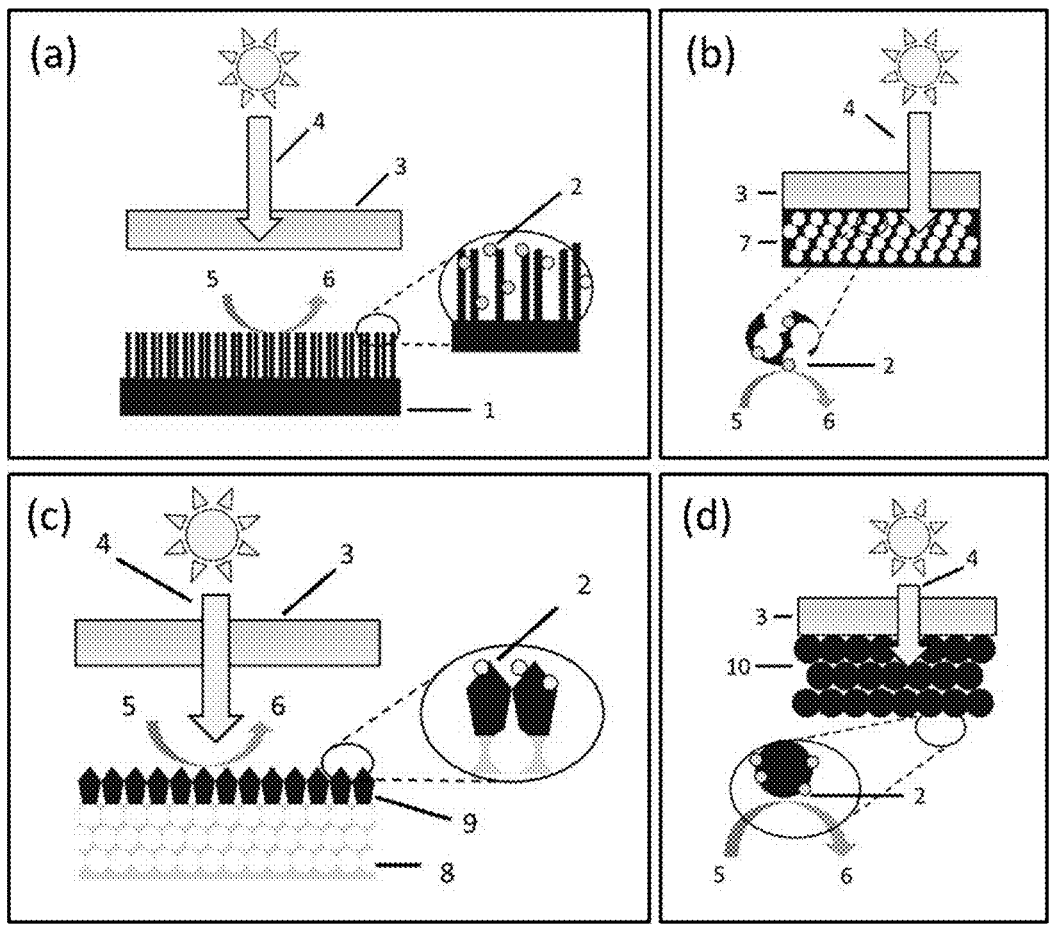
FIG. 2 shows a schematic diagram of a solar fuels reactor with glass walls and a NSSCS that is in FIG. 2(a) silicon nanowires, FIG. 2(b) an inverted silicon opal, FIG. 2(c) amorphous silicon deposited onto an inverted glass opal and FIG. 2(d) silicon nanoparticles.

Regarding $CO_2$ reduction reactions in a hydrogen environment, such as the Sabatier reaction, the valance and conduction band energies inherent to silicon are advantageous. In this context, FIG. 1 shows an energy band diagram at a junction between a p-type semiconductor and a metal. In FIG. 1 the relative positions (with respect to the vacuum energy level EVac) of the semiconductor valence band (VBS/C), conduction band (CBs/c) and the work function of the semiconductor ($\varphi_{s/c}$) and metal ($\varphi_m$) are representative of a junction formed between silicon and ruthenium. The $H_2/H^+$ redox potential energy is also shown on the diagram (denoted as $H_2/H^+$). A key feature in FIG. 1 is that the $H_2/H^+$ redox potential resides between $VB_{S/C}$ and $CB_{S/C}$. This is important because photons absorbed in the semiconductor (denoted as hv) create photogenerated holes in the valence band (denoted as $h^+$) with energy less than the $H_2/H^+$ redox potential energy and energetic electrons in the conduction band with energy greater than the $H_2/H^+$ redox potential energy (denoted as $e^-$). Thus, it is energetically possible for photogenerated electrons and holes from the silicon conduction and valence bands, respectively, to transfer to the $H_2/H^+$ redox pair. This transfer of excited charge carriers creates a chance of putting hydrogen atoms into a favorable chemically active form. A schematic illustration of a silicon nanowire support loaded with a catalyst and integrated into a solar fuels reactor is shown in FIG. 2a. In FIG. 2a a silicon nanowire support (1) is shown with a metallic or semiconductor catalyst affixed to its surface (2). The catalyst is enclosed in a reactor made from a material that is transparent to solar irradiation such as a glass wall (3). Concentrated solar light (4) is focused onto the catalyst. Gaseous reactants (5) are converted to gaseous products (6) in accordance with the chemical reactions listed in Table 1.

Amorphous silicon has a larger band gap than crystalline silicon and consequently absorbs less solar radiation. However, the material costs associated with covering large areas with amorphous silicon are much less than they are for crystalline silicon. Further, the reflection from an amorphous silicon surface can be reduced to just a few percent by introducing appropriate nanostructures into its surface. As one example, an inverted silicon opal with air holes having a diameter of approximately 100 nm exhibits minimal reflection and appears black. A schematic illustration of an inverted silicon opal support (7) loaded with a metallic or semiconductor catalyst (8) and integrated into a solar fuels reactor with a glass wall (3) is shown in FIG. 2b. It is also noteworthy that the air-holes in the inverted opal are connected which facilitates the flow of gaseous reactants and products through the structure.

Another method of fabricating an amorphous silicon film with minimal reflection and with an interconnected network of void pores is to deposit the film on top of an inverted glass opal. In this instance minimal reflection is achieved when the diameter of the air-holes in the inverted glass opal is approximately 200 nm. In this instance the thickness of the amorphous silicon film itself is on the order of 500 nm. A schematic illustration of an inverted silica opal (8) with an amorphous silicon film deposit on top of it (9) loaded with a catalyst (2) and integrated into a solar fuels reactor is shown in FIG. 2c.

Another form of nanostructured silicon that can serve as a NSSCS for solar powered photocatalysts is a thin-film comprised of nanocrystalline silicon nanoparticles. The size and shape of the nanoparticles can be tailored to minimize reflection losses while maximizing absorption losses. Furthermore, these nanoparticles can potentially be doped n- or p-type in order to tailor their electronic properties to facilitate the transfer of excited charge carriers to catalysts loaded onto their surface. A schematic illustration of a silicon nanoparticle film (10) loaded with a catalyst (2) and integrated into a solar fuels reactor is shown in FIG. 2d.

Another key advantage of the silicon NSSCS disclosed herein is that the electronic band edges of silicon are advantageously positioned to straddle the hydrogen redox potential. That is, with respect to the normal hydrogen electrode, the valence and conduction band positions of silicon are approximately $-0.5V$ and $+0.5V$, respectively. Thus, when EHPs are photogenerated in Si, electrons can readily transfer from adsorbed hydrogen to the valence band in the nanostructured support to create protons that can participate in chemical reactions. Likewise, photogenerated electrons in the Si conduction band can readily transfer to adsorbed hydrogen to create active hydrogen species. The following non-limiting examples are included to further illustrate the nano-structured solar selective catalytic support:

EXAMPLES

Example 1: Efficient Photomethanation of Gaseous $CO_2$ on Black Silicon Nanowire Catalyst Supports with Visible and Near-Infrared Photons This example describes the fabrication and performance of Ru-based nanoparticle catalysts supported on silicon nanowire supports (Ru/SiNW) that exhibit photoactivity towards the Sabatier reaction when irradiated with a broadband source including UV-, visible and NIR photons. Specifically, at a constant temperature of 93° C., the Sabatier reaction proceeds five times faster when irradiated with photons between the spectral region of 615 nm and 1100 nm as compared to tests performed at the same temperature in the dark. Furthermore, when the Ru/SiNW catalyst is irradiated with photons in the NIR spectral range (850 nm<$\lambda$<1100 nm) the reaction rate is more than twice that of the dark reaction rate. This is the first demonstration that the Sabatier reaction can be photoactivated using near-infrared photons with energy 1.1 eV<$h\upsilon$<1.5 eV.

Silicon nanowires were fabricated using a metal-assisted chemical etching (MaCE) technique. p-type silicon wafers were cut into 1 inch squares and then cleaned with ethanol, acetone and de-ionized water. The wafers were further cleaned with piranha solution ($H_2SO_4$:$H_2O_2$=3:1 by volume) for 3 hours and then rinsed with de-ionized water. Subsequently, the wafers were immersed in an etching solution consisting of 5 M HF, 0.02 M $AgNO_3$, and 3 mL of 10% HF solution in order to remove surface oxides. The solution is then placed in an autoclave and allowed to etch for one hour at room temperature. After the etching process, silver dendrites covered on the silicon nanowires were washed off with de-ionized water. To ensure all the silver nanoparticles and dendrites were removed the etched wafers were placed in concentrated nitric acid (18 M $HNO_3$) for 30 minutes. The etched wafers were then washed and dried before being cut into 1 $cm^2$ pieces. Eagle XG and p-type polished silicon wafers were cleaned in a solution of sulfuric acid/hydrogen peroxide (3:1 v/v) and then rinsed with distilled water. Ru was sputtered onto these samples which were subsequently cut into 1 $cm^2$ squares.

The sputtering deposition was carried out in a custom-built sputtering system (Kurt J. Lesker Co.) by radio frequency (RF) magnetron sputtering using a 99.95% pure Ru sputtering target purchased from Angstrom Sciences, Inc. The base pressure of the sputtering chamber was pumped down to $1 \times 10^{-7}$ Torr before Argon was introduced into the chamber at a flow rate of 20 sccm. The chamber pressure was set to 3 mTorr during the deposition, which was carried out at room temperature. The forward power was 100 W and the substrate-to-target distance was 14 cm. The sputtering process was terminated when 10 nm of Ru, as measured from an in-situ thickness monitor (SQM-242 from Sigma), had been deposited. Also, Ru was deposited on glass and polished Si control samples during the same deposition.

Figure 3:
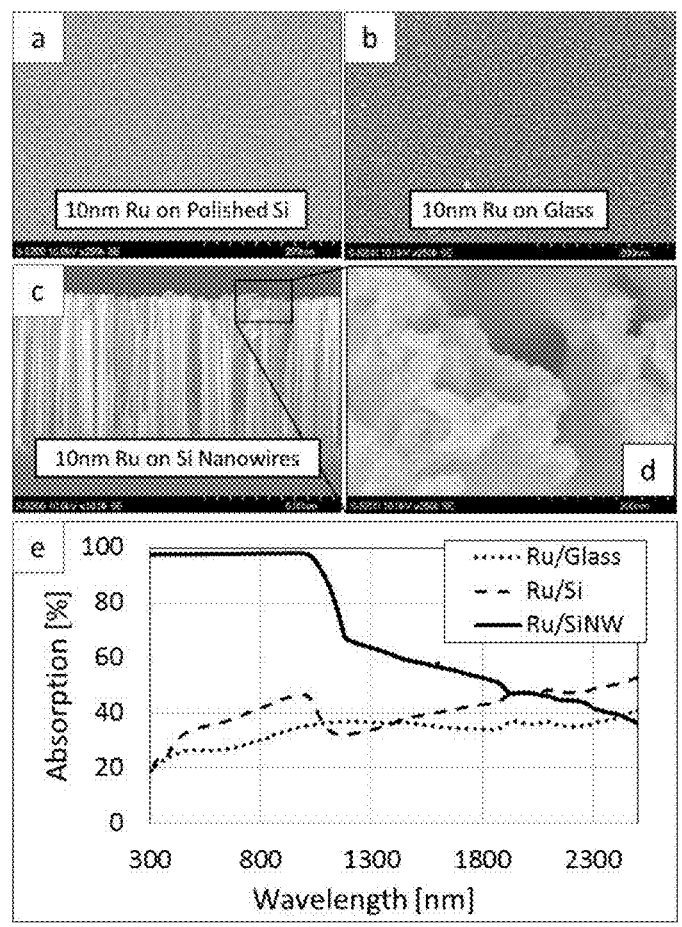
FIG. 3 shows an SEM image of 10 nm of Ru sputtered onto FIG. 3(a) a polished silicon wafer, FIG. 3(b) a glass substrate and FIG. 3(c, d) silicon nanowires.

SEM images of the polished Si, Eagle XG glass, and SiNW with Ru sputtered onto their surfaces are shown in FIGS. 3a, 3b, and 3d, respectively. A cross-sectional SEM image of the Ru/SiNW catalyst is also shown in FIG. 3c, and the SiNWs are about 100 nm in diameter and approximately 6 μm in length. The sputtered Ru resides primarily at the top of the SiNWs and no Ru is present at the base of the SiNWs next to the Si wafer. The absorption spectra for these Ru/SiNW, Ru/glass and Ru/silicon catalysts are shown in FIG. 3.

Figure 4:
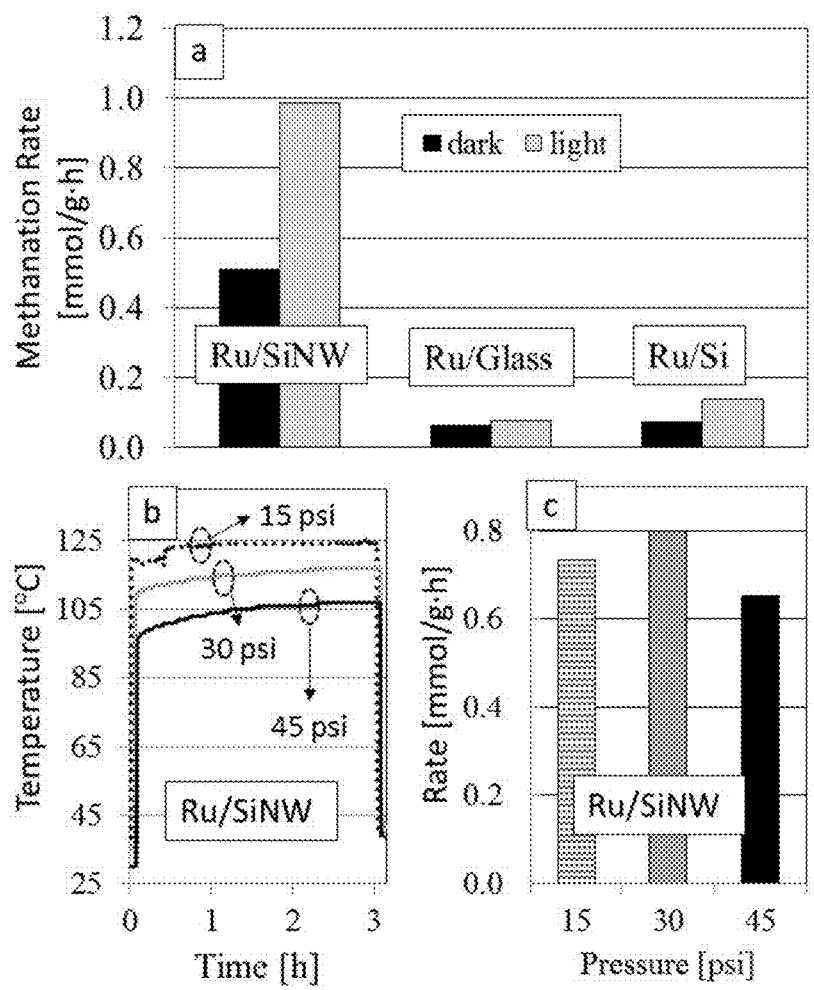
FIG. 4(a) shows the methanation rates over Ru-based catalysts on the SiNW, glass and polished Si supports at 150° C. and 45 psi.
FIG. 4(b) Shows the temperature profiles recorded for batch reactions performed at 15, 30 and 45 psi
FIG. 4(c) shows the corresponding methanation rates.

The photoactivity of the Ru/SiNW, Ru/glass and Ru/Si catalysts were initially tested at a temperature of 150° C. under solar simulated light from a Xe lamp over duration of 6 hours. The lamp intensity was 3.2 suns and the irradiated area of each sample was 1 $cm^2$. The $H_2$:$CO_2$ gas ratio was 4:1 at a pressure of 45 psi and the results are plotted in FIG. 4a. The Sabatier reaction proceeded at a rate of $6.18 \times 10^{-2}$ mmol/g·h over the Ru/glass sample in the dark and $7.52 \times 10^{-2}$ mmol/g·h when irradiated with the Xe lamp. $CO_2$ methanation rates over the Ru/Si sample increased by 84% from $7.44 \times 10^{-2}$ mmol/g·h in the dark to 0.14 mmol/g·h in the light. However, $CO_2$ methanation rates were the highest over the Ru/SiNW catalyst, proceeding at a rate of 0.51 mmol/g·h in the dark and increasing by 94% to 0.99 mmol/g·h in the light. Control experiments were also performed to show that bare SiNW without Ru were not active towards the Sabatier reaction (results not shown). Having verified the photoactivity of the Ru/SiNW catalyst at 150° C. a second set of experiments were carried out to investigate the activity of this catalyst when exposed to solar simulated light without supplemental heating from an external source. That is, the heater was disconnected and the temperature of the Ru/SiNW catalyst was monitored under the Xe lamp at an intensity of 14.5 suns. Moreover, to gain insight regarding the degree of conductive and convective cooling from the gaseous reactants, batch reaction tests were performed using a $H_2$:$CO_2$ gas ratio of 4:1 at 15, 30 and 45 psi and the temperature profiles over the three hour duration of these tests are plotted in FIG. 4b. For each run the temperature of the sample increased rapidly at the beginning of the test when the Xe lamp was turned on and then continued to rise gradually over the duration of the reaction until the lamp was switched off at the three hour point. It is also noteworthy that the sample temperature of the reactions runs at 15, 30 and 45 psi reached a maximum temperature of 125° C., 117° C. and 107° C., respectively. As was expected, raising the reactor pressure increased the amount of conductive and convective cooling thereby decreasing the maximum temperature attained by the Ru/SiNW catalyst. The $CO_2$ methanation rates corresponding to the reactions carried out at 15, 30 and 45 psi are plotted in FIG. 4c. While the $CO_2$ methanation rates were comparable for the three different pressures, within about 20% of each other, a maximum methanation rate of 0.80 mmol/g·h was measured at a pressure of 30 psi. It is known that the Sabatier reaction rate increases with increasing pressure of the reactant gases, however as shown in FIG. 4b, in going from a pressure of 30 psi to 45 psi the catalyst temperature dropped by about 10° C. causing a decrease in reaction rates.

Figure 5:
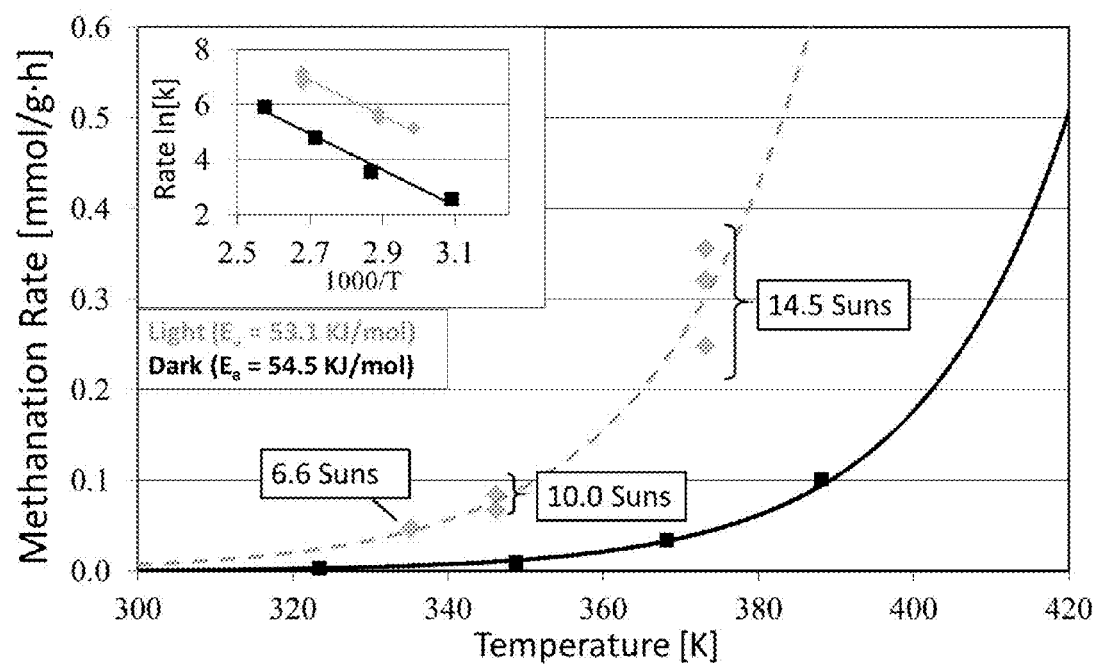
FIG. 5 shows methanation rates plotted as a function of temperature in the dark (black line) and under solar-simulated irradiation (grey line). The inset in the figure shows these methanation rates on a plot of In(k) vs 1000/T used to calculate the activation energy over the Ru/SiNW catalyst in the light and dark.

A set of experiments were performed to measure the activation energy of the Ru/SiNW catalyst. The $CO_2$ methanation rates over the Ru/SiNW catalyst in the dark are plotted as a function of temperature in FIG. 5 and the inset shows that the corresponding activation energy is 54.5 kJ/mol. This is in agreement with the activation energy reported in the literature for the Sabatier reaction when carried out over Ru-based catalysts. Furthermore, the effective activation energy under solar-simulated radiation was measured. Specifically, the heater was disconnected and a set of batch reactions were performed with varying light intensities in order to measure the Sabatier reaction rates plotted as the grey line shown in FIG. 5. Using these photomethanation rates an "effective" activation energy of 53.1 kJ/mol as shown in the inset in FIG. 5 was calculated. Thus, while the Sabatier reaction rates are greater under solar-simulated radiation, the activation energy does not differ significantly whether heating via solar-simulated radiation or a resistive heating source.

Figure 6:
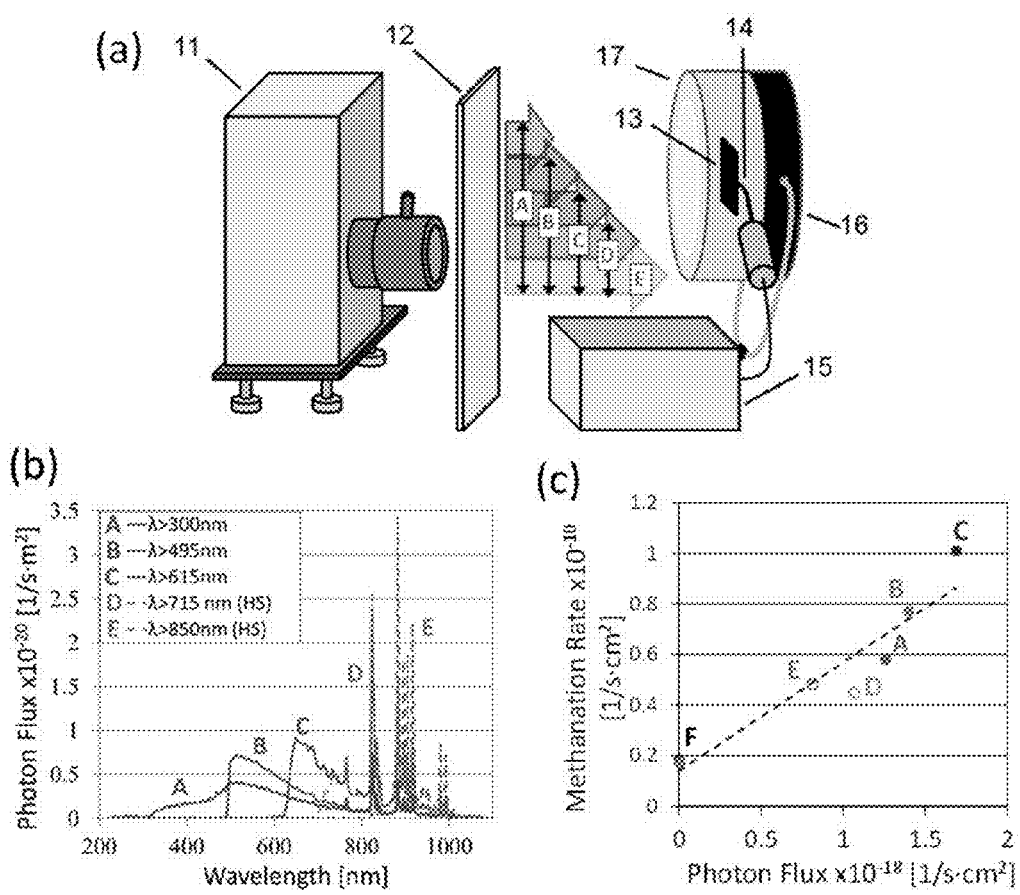
FIG. 6(a) shows a schematic representation of the experimental apparatus setup with filtered incident radiation for batch reaction tests A through E.
FIG. 6(b) shows the spectra of photons with energy greater than 1.1 eV impinging onto the Ru/SiNW catalyst for batch reactions A through E.
FIG. 6(c) shows the Sabatier reaction rate plotted as a function of the number of incident photons with energy greater than the bandgap of Silicon for the seven batch reactions performed in this set of experiments.

The fact that the activation energy is comparable, whether the Ru/SiNW catalyst was heated with solar simulated radiation or with a resistive heater, suggests that the reaction mechanism under irradiation is similar to that in the dark. However, since the reaction rates are higher under the Xe lamp, incident photons must cause some effect that accelerates the Sabatier reaction mechanism. To gain more insight into how the impinging photons accelerate the reaction rates another set of experiments were performed wherein the temperature was held constant while the incident photon flux impinging onto the Ru/SiNW catalyst was varied. This set of experiments included seven batch reactions all carried out at a temperature of 93° C., the results of which are illustrated in FIG. 6. Specifically, as shown in FIG. 6a, five of these seven tests, labelled A through E, were performed using a Xe lamp (11) and high-pass cut-off filters (12) such that for A: $\lambda>300$ nm, B: $\lambda>495$ nm, C: $\lambda>615$ nm, D: $\lambda>715$ nm, and E: $\lambda>850$ nm. For each batch reaction the intensity of the Xe lamp was adjusted such that the temperature of the Ru/SiNW catalyst (13) was always set to 93° C. The temperature was monitored using a thermocouple (14) pressed against the rear side of the Ru/SiNW catalyst. The photon distribution irradiating the Ru/SiNW catalyst for batch reactions A through E are shown in FIG. 6b. Here it can be noted that the total number of photons impinging onto the sample increases as the cut-off wavelength of the high-pass filter decreases. This is because the average thermalization energy provided to the Ru/SiNW sample is smaller for longer wavelength photons and thus more photons are required to heat the sample to 93° C. However, for cases D: $\lambda>715$ nm, and E: $\lambda>850$ nm when the Xe lamp was set to full intensity the sample reached a maximum temperature of 65° C. and 54° C., respectively. Thus, for tests D, and E, supplementary heating was supplied using a temperature controller (15) connected to a heating band (16) that was wrapped around the batch reactor (17) such that the temperature of the Ru/SiNW catalyst was maintained at 93° C. for all reactions. The two other tests performed in the set of seven experiments include one test carried out in the dark and test F, wherein the Ru/SiNW catalyst was subjected only to sub-bandgap photons with $\lambda>1100$ nm. For test F the Ru/SiNW catalyst reached a temperature of 39° C. when subjected to the long wavelength radiation and supplementary heating was also provided in this case to increase its temperature to 93° C.

The Sabatier reaction rate was plotted as a function of the number of incident photons with energy greater than the bandgap of Si for the seven batch reactions performed in this set of experiments in FIG. 6c. The methanation rate for the test carried out in the dark and for test F: $\lambda>1100$ nm was about $2\times10^9$ atoms per second. This suggested that sub-band gap photons with energy less than the band-gap of silicon did not activate the Sabatier reaction photochemically. Alternatively, heat generated when sub-band gap photons were absorbed in the Ru/SiNW sample activates the Sabatier reaction thermochemically, similarly to when the heat was provided entirely from a thermal heating source. FIG. 6c also shows that the Sabatier reaction proceeds five times faster when the Ru/SiNW sample is irradiated with photons in the spectral region 615 nm$<\lambda<$1100 nm as compared to tests performed in the dark. Furthermore, when the Ru/SiNW catalyst is irradiated with photons in the near infrared spectral range (850 nm$<\lambda<$1100 nm) the reaction rate is more than twice that of the dark reaction rate. Moreover, the slope of the line in FIG. 6 is $4\times10^{-9}$ $CH_4$ molecules/photon and this suggests that only a very small fraction of incident photons induce photochemical activity in the Ru/SiNW catalyst.

Thus, the following two statements based on the results shown in FIG. 6 can be made:

(1) Photons with energy less than the band-gap of silicon absorbed in the Ru/SiNW catalyst provide thermal energy that activates the Sabatier reaction thermochemically; and (2) Photons with energy greater than the band-gap of Si generate electron-hole pairs in the Ru/SiNW.

These excited charge carriers ultimately thermalize and recombine thereby producing heat that thermochemically accelerates the Sabatier reaction. Furthermore, a small fraction of absorbed photons with sufficient energy to excite electron-hole pairs (EHPs) in the SiNW, on the order of ten out of every billion, photochemically activate the Sabatier reaction.

In this context it is important to note that the fraction of incident photons with sufficient energy to excite EHPs that photochemically activate the Sabatier reaction can be increased by optimizing the dispersion of the Ru catalyst over the SiNW support. In this example the Ru resides primarily at the upper surface of the SiNWs. The Ru dispersion can be improved by using other methods including wet impregnation, atomic layer deposition and electrodeposition to deposit Ru along the length of the SiNW.

Here it is also important to note that while the photomethanation rates are proportional to only a small fraction of incident photons, the photochemical contribution to the overall Sabatier reaction rate is significant under concentrated solar-simulated irradiation. In fact, in comparing batch reactions C and F in FIG. 6c, or in comparing the grey and black lines in FIG. 5, it is apparent that the photochemical contribution to the reaction rate over the Ru/SiNW catalyst can be as much as ×5 greater than the thermochemical contribution.

Figure 7:
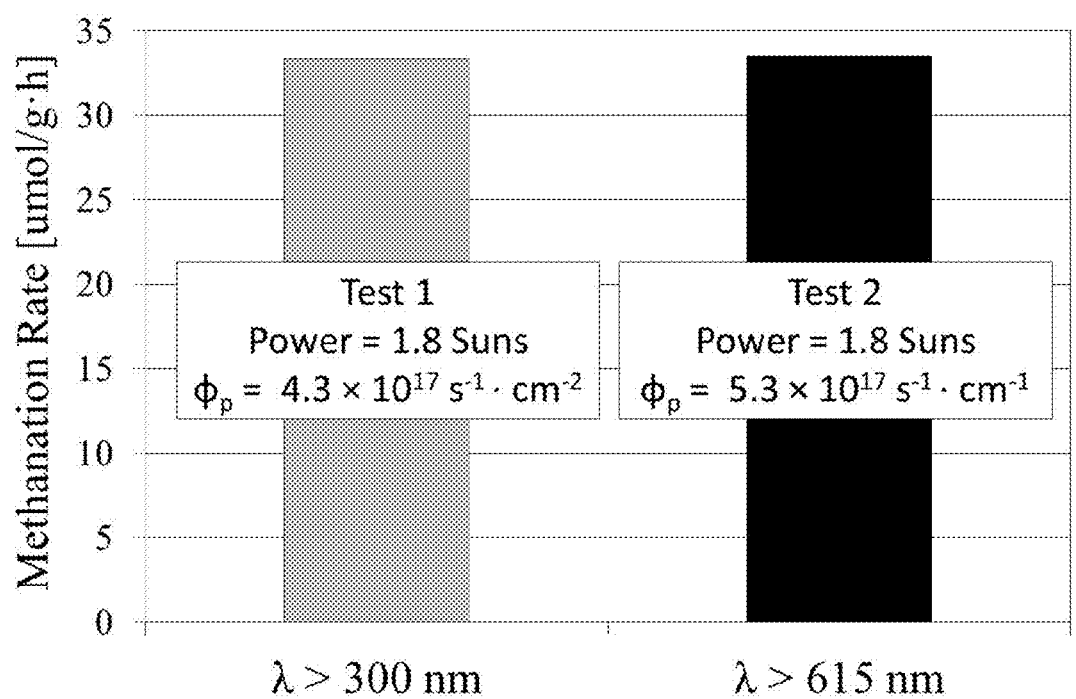
FIG. 7 shows photomethanation rates for the Ru/Glass catalyst under filtered irradiance from a 300 W Xe lamp.

It should be noted that the photochemical contribution to the overall photomethanation rate on the Ru/SiNW catalyst was not observed for the Ru/glass catalyst (see FIG. 7). Moreover, similar experiments recently reported in the literature show that photomethanation reactions on Ru-based catalysts with $Al_2O_3$ supports are driven photothermally and do not exhibit photochemical activity.[34] Thus, the photochemical activity over the Ru/SiNW catalysts disclosed herein is a unique property associated with the Si-based support.

Figure 8:
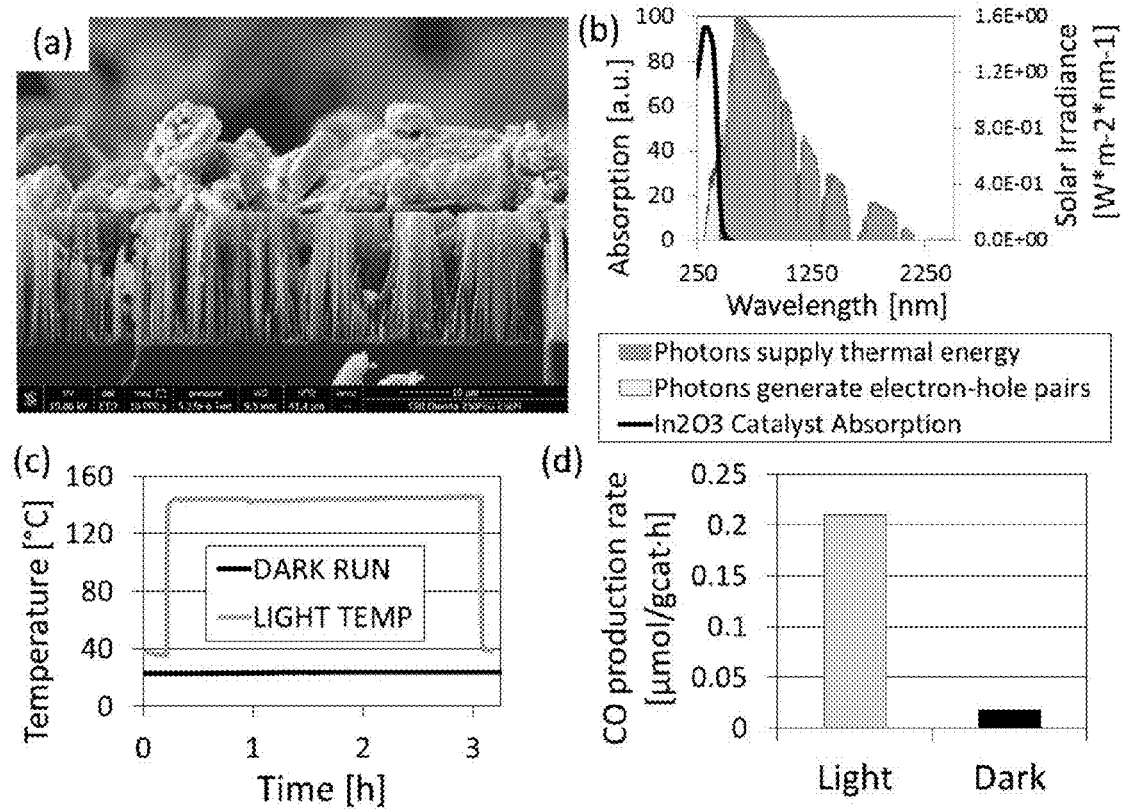
FIG. 8(a) shows a cross-sectional SEM image of $In_2O_3$ nanoparticle catalysts drop-cast onto SiNW supports ($In_2O_3$/SiNW catalyst).
FIG. 8(b) shows the relative absorption spectra of $In_2O_3$ nanoparticle catalysts (black line) superimposed over top of the AM1.5 solar irradiance.
FIG. 8(c) shows the temperature profile over the duration of the 3 hour tests carried out in the dark and under the Xe lamp.
FIG. 8(d) shows the rate at which CO is generated for these light and dark reactions.

Example 2: Silicon Nanowire Supports as a Heat Source for Solar Powered Semiconductor Nanoparticle Photocatalysts Generally speaking, SiNWs are an effective support for solar driven photocatalysts because they absorb 85% of the solar irradiance to generate EHPs across a 1.1 eV bandgap that can be used to thermochemically and/or photochemically drive solar fuels reactions. In this example SiNW supports were loaded with $In_2O_3$ nanoparticle photocatalysts that activated the reverse water-gas shift (RWGS) reaction ($CO_2+H_2 \rightarrow CO+H_2O$) under solar simulated light. A cross-sectional SEM image of the $In_2O_3$ NPs loaded onto the SiNW support is shown in FIG. 8. The band-gap of these $In_2O_3$ NPs is ~2.9 eV. Further, UV- and visible photons with wavelength less than ~430 nm can activate these nanoparticles to drive the RWGS reaction. However, the optimal reaction temperature for these $In_2O_3$ NPs photocatalysts was about 150° C. In this example it is shown that the SiNW supports can absorb incident photons with energy less than ~2.9 eV that are transmitted through the $In_2O_3$ NPs in order to generate heat required for these NPs to activate the RWGS. The relative absorption spectra of $In_2O_3$ nanoparticle catalysts (black line) superimposed over top of the AM1.5 solar irradiance[30] is shown in FIG. 8b. The grey-shaded area under the left side of the solar spectrum represents the portion of the solar irradiance that can photochemically activate the $In_2O_3$ nanoparticle catalysts while the dark colored area under the solar spectrum represents solar energy that can be used to provide thermal energy to heat the catalyst. In this experiment batch reaction tests were run to show that the $In_2O_3$ nanoparticle photocatalysts could be activated entirely by radiant energy without an external heating source. That is, the light intensity irradiated from the Xe source was increased to >15 Suns and sub-band gap photons (dark area in FIG. 8b) provided enough energy to heat the SiNW support to ~145° C. while incident photons in the UV- and visible portion of the solar spectrum (grey-shaded area) photochemically activated the reaction. The temperature profile over the duration of the 3 hour tests (measured with a thermocouple pressed against the rear side of the SiNW sample) carried out in the dark and under the Xe lamp is shown in FIG. 8c. The rate at which CO is generated for these light and dark reactions is shown in FIG. 8d. $CO_2$ reduction rates for the light run are greater than 0.2 μmol/gcat·h. This rate is in good agreement with the rates reported in the literature, although the intensity of the Xe lamp was about 2 Suns. A more intense light source was required to drive the $In_2O_3$/SiNW catalyst because the temperature of the $In_2O_3$ nanoparticles was likely significantly less than the SiNW support. That is, as shown in FIG. 8a, the $In_2O_3$ nanoparticles reside as clumps on the upper surface of the SiNWs and thermal heat transfer resistance through the $In_2O_3$ nanoparticles prevented them from reaching the same temperature as the SiNWs. Heat transfer to the $In_2O_3$ nanoparticles can be improved by increasing the contact area between the nanoparticles and the SiNW support. Nevertheless, this simple experiment demonstrates that catalyst supports can be designed to use the broadband solar spectrum to simultaneously provide thermal energy and high energy photons that photochemically activate $CO_2$ reduction reactions.

Figure 9:
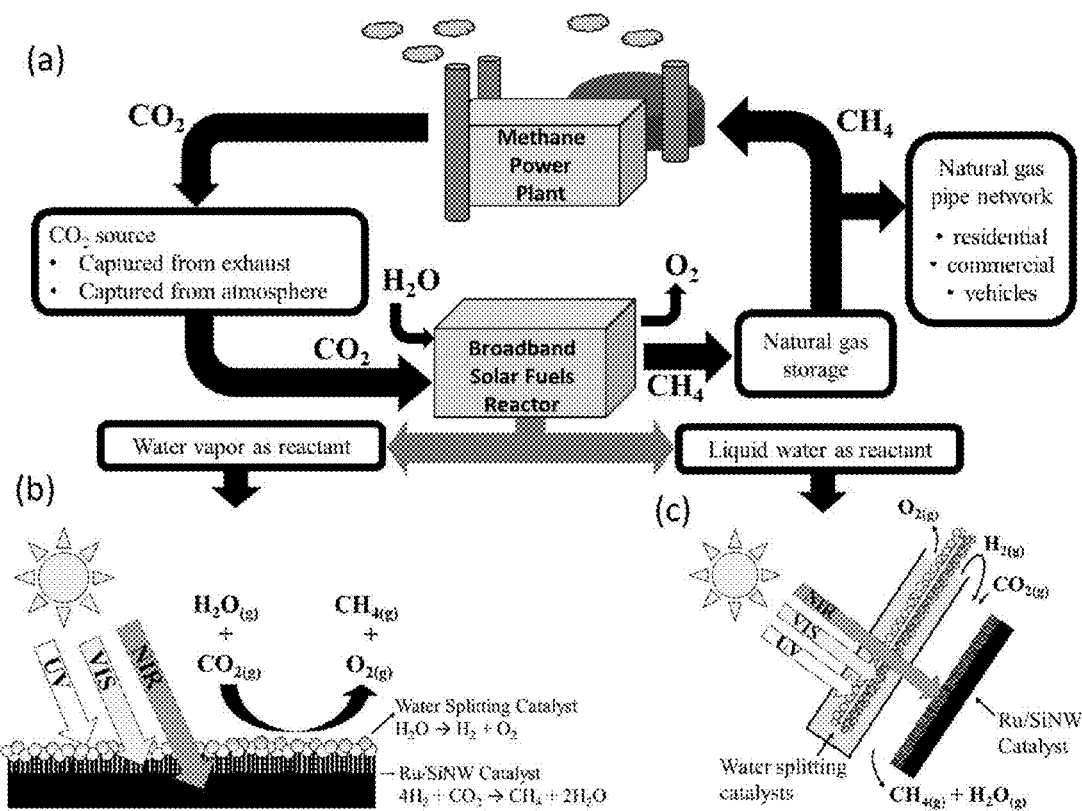
FIG. 9(a) shows a schematic diagram of a methane power plant and broadband solar fuels reactor integrated into a natural gas network cycle that recycles $CO_2$ to $CH_4$.
FIG. 9(b) Shows a schematic diagram illustrating that the idea that a thin catalyst film that utilizes UV- and Visible photons to split water can be deposited on top of the Ru/SiNW catalyst.
FIG. 9(c) shows a schematic diagram illustrating that the Ru/SiNW catalyst could be placed below a reactor that uses UV- and Visible photons to generate hydrogen from liquid water. In this tandem configuration the generated hydrogen can be exposed along with $CO_2$ across the surface of the Ru/SiNW catalyst. NIR photons transmitted through the reactor can then activate the Sabatier reaction over the Ru/SiNW catalyst.

Example 3: Broadband Tandem Solar Fuels Reactors that Split Water and Reduce $CO_2$ to Methane The ability of the Ru/SiNW catalyst shown in Example 1 to activate the Sabatier reaction using infrared photons has major implications for the design of tandem solar fuels reactors. These tandem reactors utilize the ultraviolet and visible portion of the solar irradiance to split water and generate $H_2$ which can subsequently be used to reduce $CO_2$. The general concept of this type of reactor is illustrated in FIG. 9 which shows a schematic diagram of a methane power plant and broadband solar fuels reactor integrated into a natural gas network cycle that recycles $CO_2$ to $CH_4$. The methane produced can be used for heating residential and commercial buildings and potentially transportation vehicles as well (Garthwaite, Natl Geogr, published on Sep. 4, 2013). FIG. 9b shows a schematic diagram illustrating that the idea that a thin catalyst film that utilizes UV- and visible photons to split water can be deposited on top of the Ru/SiNW catalyst. Hydrogen generated from the water-splitting reaction can be provided to the Ru/SiNW catalysts. NIR photons transmitted through the water-splitting catalyst can then be used to activate the Sabatier reaction over the Ru/SiNW catalyst. FIG. 9c shows that the Ru/SiNW catalyst could also be placed below a reactor that uses UV- and visible photons to generate hydrogen from liquid water. In this tandem configuration the generated hydrogen can be exposed along with $CO_2$ across the surface of the Ru/SiNW catalyst. NIR photons transmitted through the reactor can then activate the Sabatier reaction over the Ru/SiNW catalyst.

As shown in FIG. 6c, only a small fraction of photons impinging on the Ru/SiNW catalyst induce photochemical activity. However, under concentrated solar radiation, with an enormous flux of impinging photons, the potential to accelerate the Sabatier reaction is significant. Also, in this context it is noteworthy that optimal operating temperatures for driving the Sabatier reaction can be achieved using inexpensive parabolic trough solar concentrators. (Fernandez-Garcia et. al. Renew. Sust. Energ. Rev. 14, 1695, 2010).

Thus, the catalyst supports disclosed herein represent a key step towards the development of broadband solar fuels reactors that use the entire solar spectrum to simultaneously drive the Sabatier reaction thermochemically and photochemically. Moreover, SiNWs supports can be scaled to technologically significant proportions using well-known silicon wafer wet-chemistry processing.

LIST OF ELEMENTS

1. Silicon nanowire support
2. Metallic or semiconductor catalyst
3. Glass wall of reactor
4. Concentrated solar light
5. Gaseous reactants
6. Gaseous products
7. Inverted silicon opal support 8. Inverted silica opal
9. Amorphous silicon film
10. Silicon nanoparticle film
11. Xe lamp
12. High pass cut-off filter
13. Ru/SiNW catalyst
14. Thermocouple
15. Temperature controller
16. Heating band
17. Batch reactor

The invention claimed is:

1. A combined catalyst and catalyst support comprising:
a nanostructured solar selective support to which at least one catalyst is affixed;
the catalyst comprising at least one material that activates chemical reactions that produce fuels;
the nanostructured solar selective support comprising material that has an average absorption greater than about 80% of wavelengths ranging from about 300 nm to about 2500 nm and exhibits an overall thermal emissivity of less than about 0.35 and/or has a surface textured to lower emissivity; and
the combined catalyst and catalyst support exhibiting at least one of a photochemical effect and a photothermal effect;
wherein these effects cause the chemical reaction rates to increase with exposure to an increasing number of incident photons within the solar spectrum.

2. The combined catalyst and catalyst support according to claim 1, wherein the chemical reaction is selected from the group consisting of Sabatier reaction, methanol synthesis, reverse water gas shift, methane synthesis, carbon dioxide splitting, water gas shift, Fischer-Tropsch synthesis, water splitting, reverse Boudard reaction, dry reforming of methane, bi-reforming of methane and the Carnol process.

3. The combined catalyst and catalyst support according to claim 1 wherein the nanostructured solar selective support comprises at least one material selected from the group consisting of black silicon, black carbon, black nickel, black cobalt, black chrome, black copper, black iron, black zinc, tungsten oxide, metal silicides, and carbides.

4. The combined catalyst and catalyst support according to claim 1 wherein the nanostructured solar selective support is selected from the group consisting of
a semiconductor chosen from the group consisting of germanium, silicon, stoichiometric and non-stoichiometric metal oxides and metal sulfides;
a nanostructured solar selective support made with a pigmented selective paint;
a nanostructured silicon film made from a silicon wafer with nanowires etched into its surface;
an inverted silicon opal with an air-hole diameter ranging from approximately 50 nm to 500 nm;
a film comprised of silicon nanoparticles having a diameter on the order of magnitude of 100 nm;
a hydrogenated amorphous silicon film deposited onto a nanostructured surface; and
a silicon top surface of a photonic crystal comprising nanoscale spheres, wires, rods, tubes or nanoscale pores.

5. The combined catalyst and catalyst support according to claim 4, wherein the surface of the semiconductor support, the metallic particles or both are partially or fully oxidized.

6. The combined catalyst and catalyst support comprising a support according to claim 1, wherein the nanostructured solar selective support is made of porous silicon with an interconnected framework of pores that have a diameter on the order of 100 nm.

7. The combined catalyst and catalyst support comprising a support according to claim 1, the nanostructured solar selective support is formed from Si or SiOx nanoparticles, where x is less than 2.

8. The combined catalyst and catalyst support according to claim 1, wherein the catalyst is deposited on the support using a method selected from the group consisting of chemical vapour deposition, metal organic chemical vapour deposition, atomic layer deposition, electron beam deposition, solid phase crystallization, sputtering, wet impregnation, electrodeposition, electroless deposition, spray coating, pulsed laser deposition, electrospinning, sol-gel processes, spin-coating, dip-coating, and drop-casting.

9. The combined catalyst and catalyst support according to claim 1, wherein the catalyst comprises particles consisting of one or more metals selected from the group consisting of Sc, Ti, V, Cr, Mn, Fe, Co, Ni, Cu, Zn, Y, Zr, Nb, Mo, Ru, Rh, Pd, Ag, Cd, La, Hf, Ta, W, Os, Ir, Pt, and Au.

10. The combined catalyst and catalyst support according to claim 1, wherein the catalyst affixed to the support is a molecular complex.

11. The combined catalyst and catalyst support according to claim 1, wherein the catalyst affixed to the support is chosen from stoichiometric and non-stoichiometric main group, transition group, lanthanide and actinide group, oxides, sulfides, selenides, tellurides, phosphides, borides, carbides, nitrides, silicides, and halides and mixtures thereof.

12. The combined catalyst and catalyst support according to claim 1, wherein the catalyst affixed to the support has a shape selected from the group consisting of solid and hollow versions of spherical, cylindrical, disks, platelets, rhombic, elongated rhombic, hexagonal, square, triangular, tetrahedral, octahedral and pyramidal shapes.

13. The combined catalyst and catalyst support according to claim 1, wherein the catalyst affixed to the support is Ru or Ni particles and the catalyst support is black silicon nanowires etched into a silicon wafer.

14. The combined catalyst and catalyst support according to claim 1, wherein the catalyst support is a semiconductor with conduction and valence band energies that are about 3.5 to 4.25 eV and 4.7 to 5.5 eV below the vacuum energy level, respectively.

15. The combined catalyst and catalyst support according to claim 1, wherein the catalyst support is a semiconductor with band-gap energy between 0.3 eV and 2.5 eV.

16. A method for producing fuels by conducting a chemical reaction that produces fuels in the presence of a combined catalyst and catalyst support as claimed in claim 1 in the presence of sunlight.

17. A method as claimed in claim 16, wherein the catalyst affixed to the support is Ru or Ni particles and the catalyst support is black silicon nanowires etched into a silicon wafer.

18. A method as claimed in claim 16, wherein the catalyst support is a semiconductor with conduction and valence band energies that are about 3.5 to 4.25 eV and 4.7 to 5.5 eV below the vacuum energy level, respectively.

19. A method as claimed in claim 16, wherein the catalyst support is a semiconductor with band-gap energy between 0.3 eV and 2.5 eV.

20. A nanostructured solar selective support to which at least one catalyst can be affixed, comprising material that has an average absorption greater than about 80% of wavelengths ranging from about 300 nm to about 2500 nm and exhibits an overall thermal emissivity of less than about 0.35 and/or has a surface textured to lower emissivity.

* * * * *